United States Patent [19]
Malmin

[11] Patent Number: 5,078,604
[45] Date of Patent: Jan. 7, 1992

[54] DENTAL BARRIER DRAPE DEVICES AND RETAINER APPARATUS THEREFOR

[76] Inventor: Oscar Malmin, 3621 Federal Way, Boise, Id. 83705

[21] Appl. No.: 485,124
[22] Filed: Feb. 26, 1990
[51] Int. Cl.$^5$ ............................................. A61C 5/12
[52] U.S. Cl. ..................................... 433/138; 433/136
[58] Field of Search ............... 433/136, 137, 138, 139, 433/140

[56] References Cited

U.S. PATENT DOCUMENTS

| | | | |
|---|---|---|---|
| 1,579,608 | 4/1926 | Haudenshield | 433/137 |
| 1,604,136 | 10/1926 | Stoloff | 433/137 |
| 4,544,357 | 10/1985 | Williams | 433/136 |
| 4,721,465 | 1/1988 | Barasz | 433/137 |

Primary Examiner—Cary E. O'Connor

[57] ABSTRACT

A preformed dental barrier drape contoured to conform to the normal human oral cavity, including indices for cutting perforations to expose either one or a plurality of teeth at the crown, to include the sides and/or neckline and adjacent gingival tissue is provided. When positioned in a pateint's mouth, the dental barrier drape is draped over the teeth and other structures and features of the oral cavity with sufficient barrier material removed at required locations to expose the teeth and gum areas to be operated on. The barrier drape device may include an integral formable perimeter support structure and integral support structures along the alveolar arches. Various barrier drape retaining devices to retain the barrier device in position and seal the barrier drape material to the teeth at the neckline of a tooth are described.

30 Claims, 13 Drawing Sheets

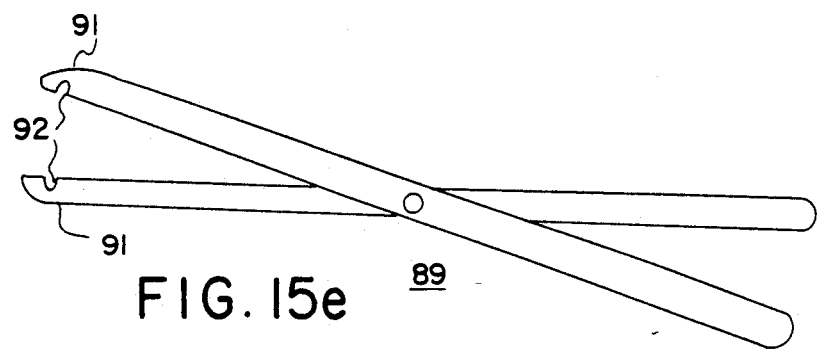
FIG. 15e
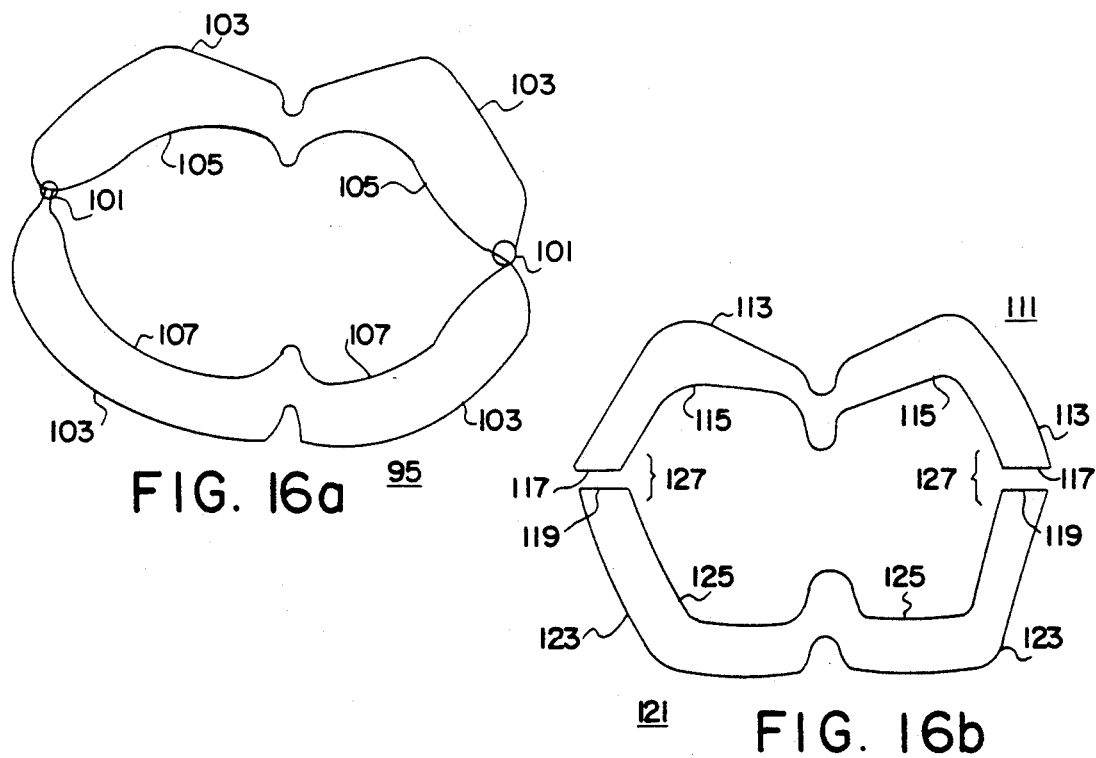
FIG. 16a
FIG. 16b

DENTAL BARRIER DRAPE DEVICES AND RETAINER APPARATUS THEREFOR

BACKGROUND OF THE INVENTION

The present invention relates generally to dental appliances and more particularly to preformed, contoured dental oral barrier drape devices for isolating particular portions of a patient's mouth and teeth and to various corresponding retaining devices for maintaining the placement of such barrier drape devices.

When performing dental procedures such as crown and cavity preparations, and restorations, bonding and the like, it is well known in the art to utilize cotton rolls to isolate particular areas of a patient's mouth or oral cavity. The cotton rolls are used either loosely placed, or held in position by various clamping devices. As such, cotton rolls do not effectively preclude the accumulation of saliva over prolonged periods of operating time, nor do they isolate the operating area from moisture and bacterial contamination from the patient's breath. Further, cotton rolls do not guard or shield the throat and vulnerable respiratory tree and alimentary tract from foreign objects or debris.

To control and hold back, "dam", the saliva while effectively isolating a desired tooth, or group of teeth, it is well known in dental clinical practice to employ a thin, flat sheet of rubber material, a dam, to isolate the site to be operated upon from the remainder of a patient's mouth. In practice, the rubber dam is perforated by the practitioner in the pattern required to expose the operating site and the tooth (teeth) to be operated on. The perforated rubber dam is inserted into the patient's mouth and the perforated portions are stretched and forced down over the crown(s) of the tooth (teeth). The peripheral edges of the rubber dam are secured to an external frame to control the excess rubber dam material. Clamps or ligatures are attached to the neckline(s) of the tooth (teeth) over and superior to the surface of the rubber dam thereby preventing the rubber dam from slipping up over the crown(s) and off of the tooth (teeth).

Typically, the frame is external to the patient's mouth and lays against the patient's chin and/or cheeks. The rubber dam serves to isolate the teeth and the operating site from the moisture and bacterial contamination from the patient's breath. It further serves to prevent ingestion and/or aspiration by the patient of debris and foreign objects. Such prior art dental barrier devices are exemplified by the following U.S. patents.

U.S. Pat. No. 174,942 issued Mar. 21, 1876 to Parmly Brown discloses the use of a dental rubber dam having premolded concave depressions of oval or other convenient shape to suit the locations of the different teeth. The molded concave shape of Brown provides a depression in the rubber dam material which fits in the floor of the mouth or palate to relieve some of the puckering and wrinkling encountered with flat rubber dam material. However, this device provides no guidelines for isolation of individual or groups of teeth and fails to seal off the remainder of the oral cavity and protect the patient's throat and airway from operating debris, dental instruments or inadvertently dislodged devices.

U.S. Pat. No. 741,890 issued Oct. 20, 1903 to Henry Craigie discloses a rubber dental dam having annular rings or thickened borders formed in the dam material surrounding each intended perforation for the isolation of each tooth. The purpose of these annular rings is to act as clamping means in order to affix the dam to the exposed teeth. The annular rings are cumbersome to fit, tend to ride up over the teeth and place too much dam material in the interproximal regions. The device prevents full preparation of the crown portion of the tooth as the annulus portion of the dam material obscures the neckline areas of the tooth and gum.

U.S. Pat. No. 1,579,608 issued Apr. 6, 1926 to Samuel S. Haudenshield discloses a rubber dental dam having indicia printed or embossed on flat rubber dam material depicting the occlusal incisal surfaces of a full dentition to serve as a guide for the practitioner to punch perforations to expose the teeth at the operating site. While the indicia aid in exposing the operating site, because the indicia do not provide for irregularities in arch form and tooth position, punching in the indicated positions may make placement and installation of the rubber dam difficult and affect the effectiveness of the seal.

U.S. Pat. No. 2,092,549 issued Sept. 7, 1937 to John M. Craigo discloses the use of a preformed cup-shaped partial rubber dam designed to be utilized with only a few teeth in either arch. This appliance serves to isolate only the several teeth at the operating site and fails to seal off the remainder of the oral cavity and does not protect the patient's throat and airway from the debris formed by the operating procedure, dental instruments or inadvertently dislodged devices such as clamps or wedges.

Flat sheet dental rubber dams are difficult to place due to the resilient nature of the materials utilized. A flat sheet does not easily adapt to the complexities and varieties of curvatures and contours of the human oral cavity, such as the alveolar ridges supporting the teeth, the vestibules of the cheeks and lips, the floor of the mouth and the palate. Further, the resilient nature of the rubber dam material exerts a tension in the material when stretched over a tooth or teeth to be exposed and requires the use of strong, spring steel clamps to retain the rubber dam in position over a tooth. In addition to the tendency of the rubber dam to slip off of a tooth, the use of an external peripheral frame creates additional tension in the dam material which also tends to lift the clamping device off of the tooth thereby releasing the dam.

To retain prior art flat sheet rubber dams in place, a large variety of metal clamps having different forms and designs are available. Generally such metal clamps are formed of spring steel and have jaws with sharp edges and points which bite into the tooth at the tooth neckline above or superior to the surface of the dam material and retain the rubber material down below the neckline of the tooth. Such clamps are difficult to position requiring special instruments such as forceps, to hold and place them in a patient's mouth. Further, such clamps are often painful to the patient due to sensitive root surfaces. The clamps can incise the gingival tissues and chip or cut the surface of the root thus damaging the tooth. A likelihood exists that the clamps may become detached and inadvertently be ejected from the mouth or into the throat of the patients where they have been known to lodge in the trachea and lungs or the alimentary canal and stomach. To insure that such mishaps do not occur, it is necessary to attach a length of cord to each clamp to prevent loss or swallowing of a clamp should it inadvertently become loose in the patient's mouth.

Prior art dental rubber dam devices are difficult and time consuming for the practitioner to install and relatively uncomfortable for the patient. Further, the need for extremely high clamping forces to maintain the tensioned rubber dam in position can require the use of clamps which can damage the teeth and pose a potential life-threatening hazard to the patient. For these reasons many practitioners do not use the presently available rubber dam devices and risk the patient inadvertently aspirating or ingesting dental debris and instruments and unnecessary exposure to themselves of infection transmittal from the patient, such as various forms of hepatitis, respiratory infections and acquired immune deficiency syndrome (AIDS), as well as potential liability if the patient accidentally ingests foreign material such as the operating debris or a dental device.

SUMMARY OF THE INVENTION

The present invention provides a unitary, preformed, contoured, elastomeric, oral barrier device which can be quickly installed in the oral cavity and draped over the teeth and over structures of the oral cavity to isolate the operational site and to protect the patient's throat from the accidental ingestion or aspiration of operating debris, irrigating solutions, other fluids, dental instruments, appliances or other dental devices. The oral barrier device of the present invention simultaneously provides distinctive means or indicators of predetermined position for the incisions, perforations or removal of barrier material to expose the desired number of teeth to be operated on, while isolating the exposed teeth from the rest of the oral cavity. While such indicators or guides are illustrated in a convex form herein, concave indicator forms, or stamped, embossed or printed indicators can be used, if more suitable for the manufacturing process. The preformed, contoured oral barrier may be used in a form employing a separate external perimeter support and control frame, or may incorporate an integral perimeter support and control frame. It may further incorporate either an integral beading, arch or frame for the alveolar ridges with all such supportive and control means fabricated of malleable or formable material, so that the practitioner can better fit the oral barrier to the oral cavity.

The present invention closely follows, or comparatively passively adapts to, the contours of the human oral cavity thereby eliminating much of the tension and rebound effect, and the bunching, puckering and wrinkling problems of a conventional flat sheet rubber dam. The preformed, contoured shape of the instant barrier device is comfortable for the patient to wear and reduces the discomfort and stress on the patient which is inherent in the high tension, harsh clamping, rigid external frame support of commonly used prior art rubber dams. A further advantage of the preformed, contoured oral barrier drape is the use of various tooth borne and tissue borne retainer devices, which avoid the stress both between the conventional rubber dam clamps that anchor the rubber dam material and the rigid external frame utilized to hold the excess rubber dam material away from the operating site. Due to the more passive nature of the preformed, contoured oral barrier of the instant barrier device, the high tension and rebound effects of the conventional stretched rubber dam material are avoided thus permitting the use of much gentler retaining pressures both in tooth borne clasps and tissue borne retainer devices thereby avoiding the risk of damage to the teeth or tissues when placed in, or removed from, the oral cavity.

Another feature of the full, preformed, contoured oral barrier drape of the present invention is the additional protection afforded to the practitioner from infection from the patient's breath and the additional protection to the patient from the debris and instrumentation of the dental operation.

The oral barrier drape of the present invention is fabricated of inexpensive and readily available materials so that it may be discarded after use on a patient to avoid any hazards of cross-contamination and the demands of effective sterilization. The oral barrier drape may be made of unflavored or slightly flavored materials to make its use more pleasant for the patient, although strong flavors are not recommended since these would promote increased salivation and discomfort for the patient.

The oral barrier drape of the present invention can be constructed in a manner that varies from a full preformed form that is contoured to the anatomy of the oral cavity to a partial, preformed, oral barrier form that is contoured to specific anatomical structures in the oral cavity. The oral barrier may also be constructed in various proportional sizes to accommodate the oral cavities sizes ranging from children to adults.

The present invention further describes various tissue, tooth or tissue and tooth borne retainer and clasping devices. The purpose of the various clasping and retainer devices is to maintain in position, stabilize and more closely adapt the preformed, contoured oral barrier drape to the underlying oral cavity anatomy and around the necklines of the exposed teeth. The tissue borne devices are those that seek stabilization and retention in the various grooves or troughs of the oral cavity. The tissue and tooth borne devices utilize both such grooves or troughs and the teeth to obtain stabilization and retention. The tooth clasping devices have free end tips designed to protrude into the interproximal spaces beneath the contact points of the teeth and obtain both vertical and horizontal retention from the anatomy of the teeth, thus maintaining the oral barrier material in close adaptation to the exposed teeth while simultaneously avoiding damage to either the teeth or soft tissues.

BRIEF DESCRIPTION OF THE DRAWINGS

FIGS. 1b-1d are a side view taken in section illustrating the alveolar ridge forms for the oral barrier drape shown in FIG. 1a.

FIG. 1e is a side view in section showing the installation of oral barrier drape of FIG. 1a.

FIG. 15e is a side view in perspective of the plier-type forceps utilized to position and remove the retainers shown in FIGS. 15a and 15b.

FIGS. 16a and 16b are a front view in perspective of another embodiment of the resilient wire retainer devices according to the principles of the present invention.

FIG. 18b is a side view in perspective of a spring accessory device to be used with the retainer device shown in FIG. 18a.

FIG. 20b is a view in perspective of a forceps-type tool to be used with the retainer device shown in FIG. 20a.

DETAILED DESCRIPTION OF THE PREFERRED EMBODIMENT

Figure 1A:
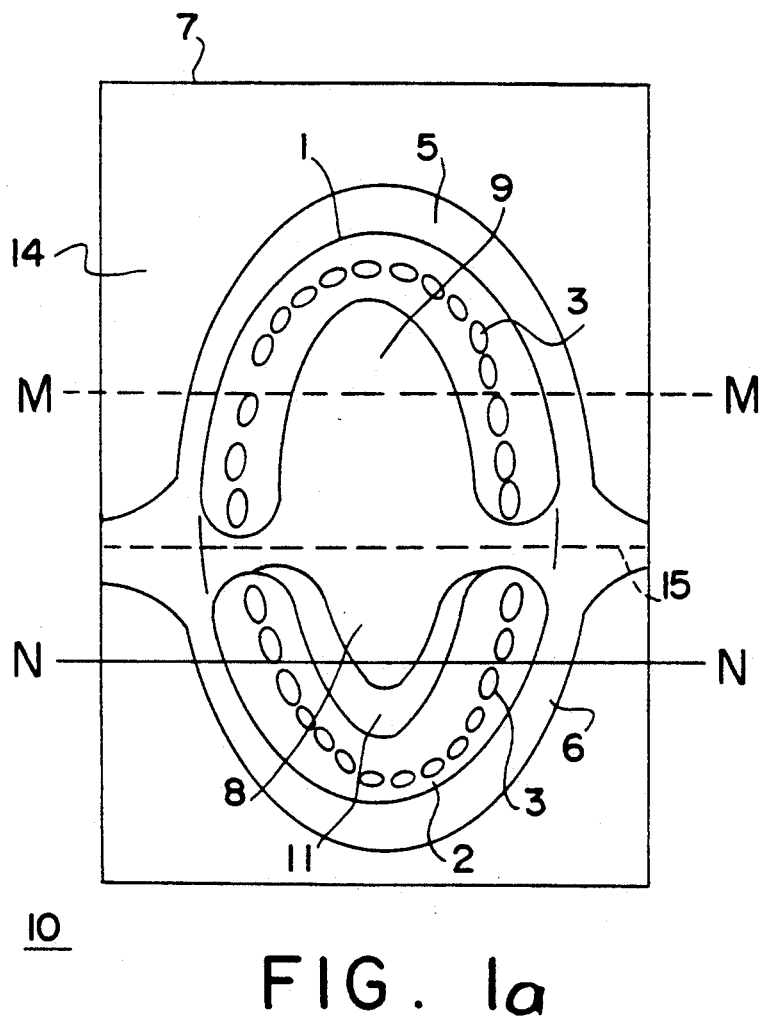
FIG. 1a is a top pictorial plan view of an opened full oral barrier drape with tooth perforation guides constructed in accordance with the present invention.
Figure 1B:
Figure 1C:
Figure 1D:
Figure 1E:
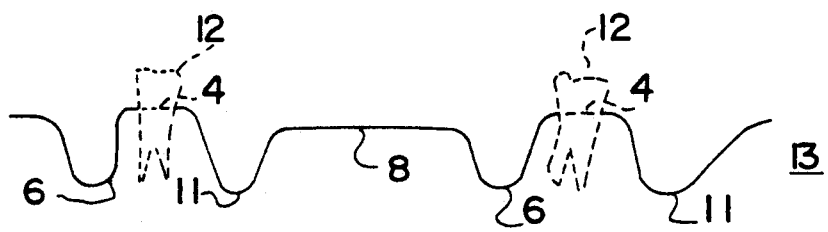

Referring now to FIGS. 1a–1e, a preformed, contoured oral barrier drape constructed according to the principles of the present invention is shown. The dental barrier drape 10 of the present invention comprises a generally rectangular shaped thin membrane of a resiliently flexible material such as natural rubber or suitable plastic having upper and lower alveolar ridges 1 and 2 and other contoured features formed therein that correspond to the various portions of the interior anatomy of a human mouth and oral cavity. The upper alveolar ridge 1 is formed in the barrier device in close adaptation to a normal human alveolar ridge, having tooth perforation guides 3 at the superior, or dorsal, portion of the alveolar ridge 1 indicating the location of normal teeth. In use, the practitioner incises a perforation utilizing the tooth perforation guide 3 which provides an opening in the alveolar ridge 1 at the relative position of and closely contoured to the neckline 4 of the tooth 12 to be exposed. The perforation guide 3 may be embossed, perforated or molded, either convex or concave, or otherwise marked configurations corresponding to the approximate size and shape of the teeth at that location. FIGS. 1b14 1d illustrate convex (FIGS. 1b-1c) and concave (FIG. 1d) forms for the perforation guides 3 and the contour of the edge 13 of the barrier drape 10 (taken in section) with respect to the neckline 4 of the tooth 12 in the alveolar ridges 1, 2. An upper buccal vestibule concavity 5 corresponding to the upper buccal vestibule extends outwardly from the alveolar ridge 1 toward the barrier drape perimeter 7. A palatal concavity 9 conforming generally to the upper palatal area of the mouth is formed in the interior of the alveolar ridge 1 to the same or lesser depth as the level of the upper buccal vestibule concavity 5. The lower alveolar ridge 2 is formed in the barrier 10 in the same manner as upper alveolar ridge 1 with perforation guides 3 indicating the location of normal teeth. A lower buccal vestibule concavity 6 corresponding to the lower buccal vestibule with the lower vestibule continues outwardly from the alveolar ridge 2 toward the barrier drape perimeter 7. The lower portion of the barrier drape 10 includes a lingual trough 11 formed in the interior of the alveolar ridge 2 that approximates the level of the lower buccal vestibule concavity 6 and rises to lingual convexity 8 to provide space for the tongue. The lingual convexity 8 blends into the distal portion of the palatal concavity 9 at the midportion of the barrier drape 10 (along dashed line 15) and diverges outwardly between the distal ends of the upper and lower alveolar ridges 1, 2 to the barrier drape perimeter 7. The barrier drape perimeter 7 features rounded corners to minimize excess material, but a skirt 14 is retained to allow the practitioner the option of folding the material up or down to accommodate specific patient oral features. While the dental barrier drape device 10 is shown in a flat configuration, in use the barrier drape device is loosely folded at its midportion along dashed line 15. FIG. 1e illustrates the contour of the barrier drape edge 13 (taken along section N—N) when the barrier drape is installed in a patient's mouth. The appropriate perforation guides 3 are cut out to provide openings corresponding to the location and shape of the tooth or teeth 12 which it is desired to expose and isolate from the remainder of the oral cavity. The edges of the apertures thus formed fit tightly about the tooth 12 at the neckline 4 while the barrier drape contour 13 drapes the buccal and lingual troughs 6, 11, respectively, on both sides of the alveolar ridge 2 and provides space 8 for the tongue. The dental barrier drape device 10 of the present invention is manufactured by well-known methods such as molding or dipping.

Figure 2:
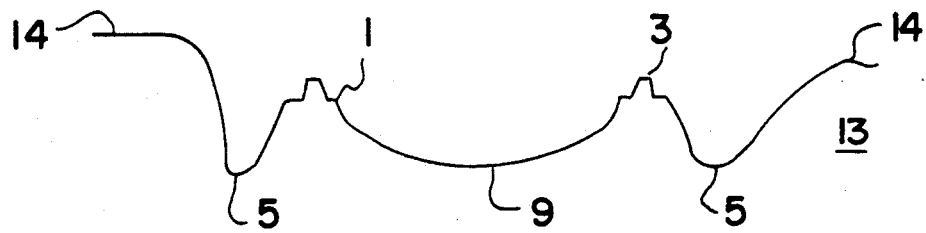
FIG. 2 is a cross-sectional view taken at line m—m' as indicated in FIG. 1 showing preferred convex forms for the tooth perforation guides.

Referring now to FIG. 2, a cross-section taken at M—M on FIG. 1a, the barrier drape edge 13 contour corresponding to the upper portion of the oral cavity is shown. The skirt 14 can be folded up or down as the practitioner desires. The upper buccal vestibule concavity 5 and the upper alveolar ridge 1 blend into the palatal concavity 9 from both sides. The upper alveolar ridge 1 is formed with convex tooth perforation guides 3, for example.

Figure 3:
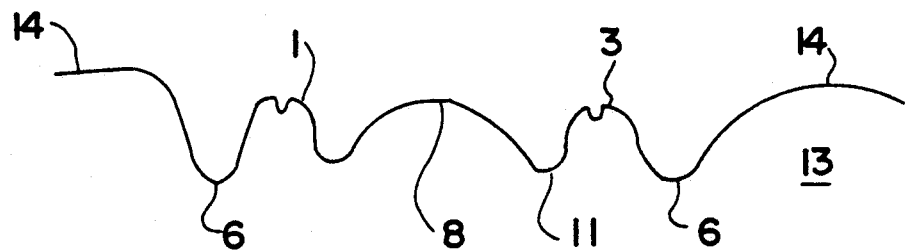
FIG. 3 is a cross-sectional view taken at line n—n' as indicated in FIG. 1 showing preferred convex forms for the tooth perforation guides.

Referring now also to FIG. 3, a cross-section N—N as indicated in FIG. 1, the barrier drape edge 13 contour corresponding to the lower portion of the oral cavity is shown. The skirt 14 blends into the lower buccal vestibule concavity 6 which adjoins the lower alveolar ridge 2 from both sides and then descends to the lingual trough 11 which rises to lingual convexity 8 to provide space for the tongue. The lower alveolar ridge 2 is formed with concave tooth perforation guides 3, for example.

Figure 4:
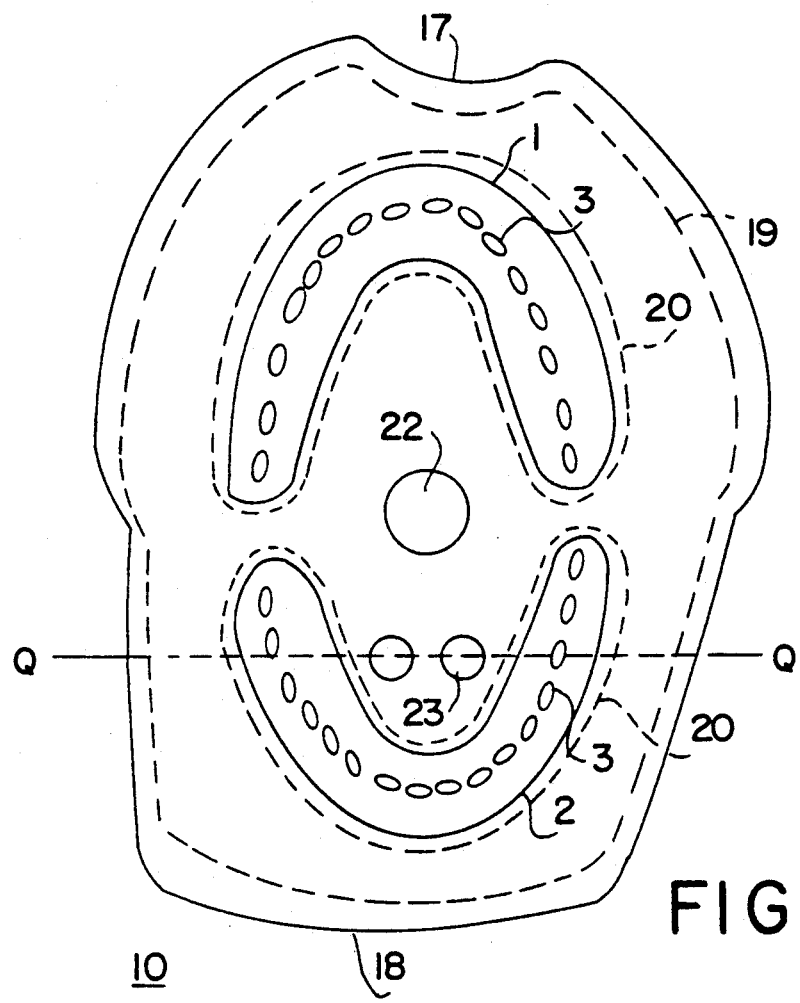
FIG. 4 is a top pictorial view of a full oral barrier drape with a tapered perimeter, tooth perforation guides, a support structure, breathing aperture perforation guide and saliva ejector aperture guides constructed in accordance with the present invention.

Referring now to FIG. 4, additional features may be incorporated into the basic design shown in FIG. 1a, as described hereinabove. The generally rectangular shape of the barrier drape 10 may be made more generally oval to conform to the shape of the mouth and face and include a nasal concavity 17 in the periphery 18 located to provide clearance for a patient's nose when the barrier is used in an opened configuration. A perimeter support structure or frame 19 may be embedded within the barrier material adjacent and around the barrier periphery 18. The frame 19 fabricated of a bendable, malleable material such as soft wire or suitable plastic allows the barrier 10 to be easily shaped to provide control of the barrier drape peripheral or skirt areas 14 for ease of access and to minimize interference with dental procedures. Similarly, such framing material may be embedded around the base 20 of the upper and lower alveolar ridges 1, 2 to allow the concave alveolar ridge forms 1, 2 to be shaped to more closely conform to the contours of an individual patient's alveolar ridge features. Alternatively, during manufacture, integrally-formed beading 21 comprising thickened areas of barrier material may be formed around the sides of the upper and lower alveolar ridges 1, 2 to provide a tighter, snugger fit thus achieving additional sealing of the barrier to the underlying alveolar ridges in the oral cavity. The beading 21 is preferably of round cross-sectional shape, but may be of any desired geometric shape such as elliptical, rectangular, x-shaped or dumbbell. A breathing aperture perforation guide 22 is provided at the barrier drape mid portion approximately midway between the upper and lower alveolar ridges 1, 2 and may be used for patients who may have difficulty breathing nasally during an operation. Similarly, saliva ejector perforation guides 23 provide location and support to retain a saliva ejector or other aspiration appliance in the lingual trough 11. The airway and saliva ejector perforation guides 22 and 23 may be concave, slightly convex or strongly convex. The tapered barrier peripheral outline 18 conforms to the shape of a patient's normal facial features. The tooth perforation guides 3 in the upper alveolar ridge 1 and lower alveolar ridge 2 are as described hereinabove.

Figure 5:
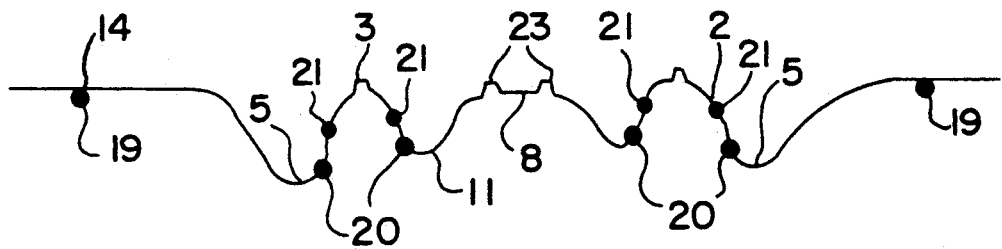
FIG. 5 is a cross-sectional view taken at line q—q' as indicated in FIG. 4 showing the convex forms for the saliva ejector apertures perforation guides.

Referring now also to FIG. 5, a cross section taken at Q—Q as shown in FIG. 4, the perimeter support structure 19 is embedded in the under side of the barrier drape material. It is to be noted that perimeter support structure 19 could also be embedded in the midpoint of the thickness of the barrier drape or on the top side without deviating from the present invention. The alveolar ridge support structure 20 at the base periphery of the alveolar ridges 1, 2 may likewise be embedded on either surface of the barrier drape material or within it. The saliva ejector perforation guides 23 are of a preferred convex shape as shown. The lingual convexity 8 and lower buccal vestibule concavity 6 are as described hereinabove.

Figure 6:
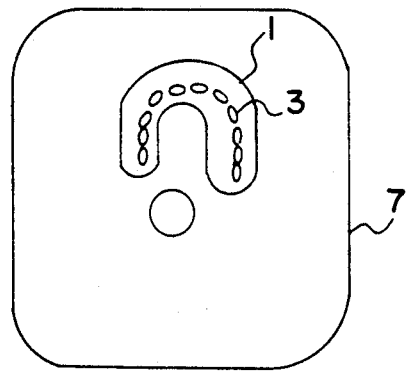
FIG. 6 is a top pictorial plan view of an opened partially formed barrier drape constructed in accordance with the present invention for a specific portion of the oral cavity showing the tooth perforation guides and the breathing aperture perforation guides.

Referring now to FIG. 6, a second embodiment of a fully dentulous barrier drape as discussed hereinabove is illustrated. In this embodiment a barrier drape device 31 for a full upper alveolar ridge 1 having rounded peripheral corners includes alveolar support structure 20 and breathing aperture perforation guide 22. The features of the fully dentulous barrier drape device 10 as discussed with reference to FIGS. 1 and 4 above may also be incorporated in the upper alveolar barrier drape 31 of this embodiment.

Figure 7:
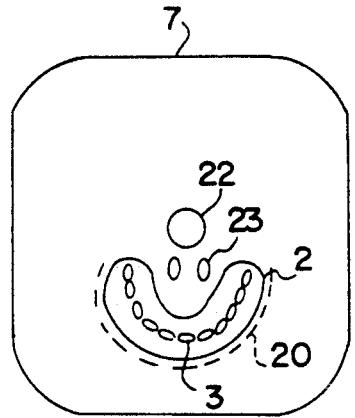
FIG. 7 is a top pictorial plan view of an opened partially formed barrier drape constructed in accordance with the present invention for a different specific portion of the oral cavity showing the tooth perforation guides and the saliva ejector apertures.

Referring now to FIG. 7, a third embodiment of a fully dentulous barrier drape as discussed hereinabove is illustrated. In this embodiment a barrier drape 33 for a full lower alveolar ridge 2 having rounded peripheral corners includes alveolar support structure 20 and saliva ejector perforation guides 23. The features of the fully dentulous barrier drape 10 as discussed in reference to FIGS. 1 and 4 above may also be incorporated in the lower alveolar barrier drape 33 of this embodiment.

Figure 8:
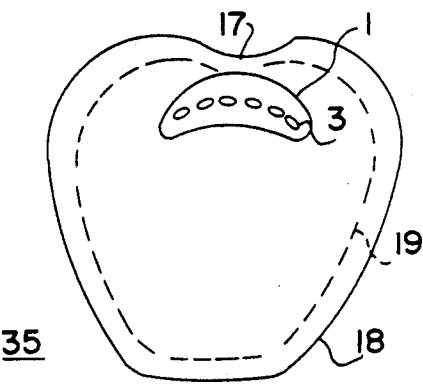
FIG. 8 is a top pictorial plan view of an abbreviated oral barrier drape device constructed in accordance with the present invention showing a partial identification form for operation on the upper teeth.

Referring now to FIG. 8, a fourth embodiment of a fully dentulous barrier drape as discussed hereinabove is shown. In this embodiment, a barrier drape 35 for an upper anterior sextant having a shaped perimeter 18 and nasal indentation 17 and support strucure 19. The features of the fully dentulous barrier drape 10 as discussed with reference to FIGS. 1 and 4 above may also be incorporated in this embodiment.

Figure 9:
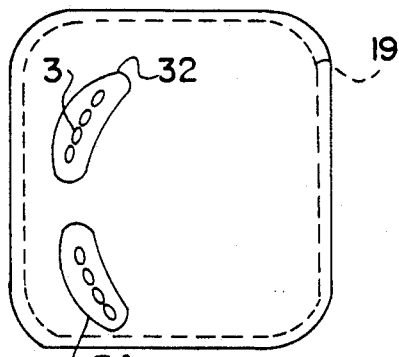
FIG. 9 is a top pictorial plan view for a partially preformed oral barrier drape constructed in accordance with the present invention showing a combination of upper and lower identification perforation guides.

Referring now to FIG. 9, a fifth embodiment of a fully dentulous barrier drape as discussed hereinabove as shown. In this embodiment, a barrier drape 37 having rounded peripheral corners for a unilateral upper 32 and lower quadrant 34 dentulous pattern includes a perimeter support structure 19. The features of the fully dentulous barrier drape 10 as discussed with reference to FIGS. 1 and 4 above may also be incorporated in this embodiment.

Figure 10:
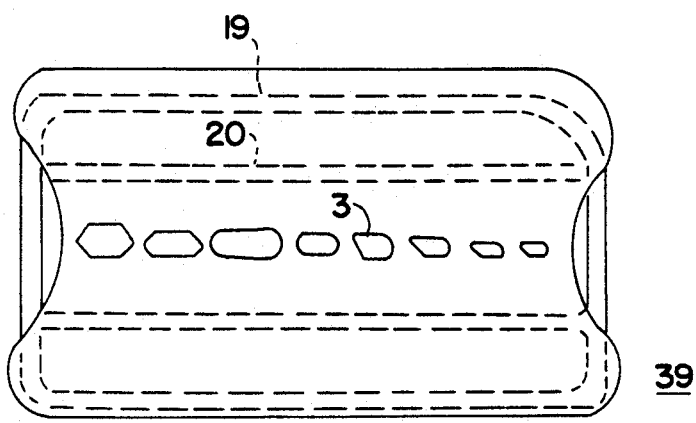
FIG. 10 is a miniaturized oral barrier drape for a portion of the oral cavity, showing the support structure and preformed indices for the teeth.

Referring now to FIG. 10, an abbreviated dental barrier drape 39 may be constructed using the principles of the present invention to meet specific needs of the practitioner. In this illustration, upper alveolar ridge 1 or lower alveolar ridge 2 for a portion of the total dental arch is isolated by alveolar support structure 20 and perimeter support structure 19 to form a barrier drape for operation on the associated teeth and gums.

Figure 11:
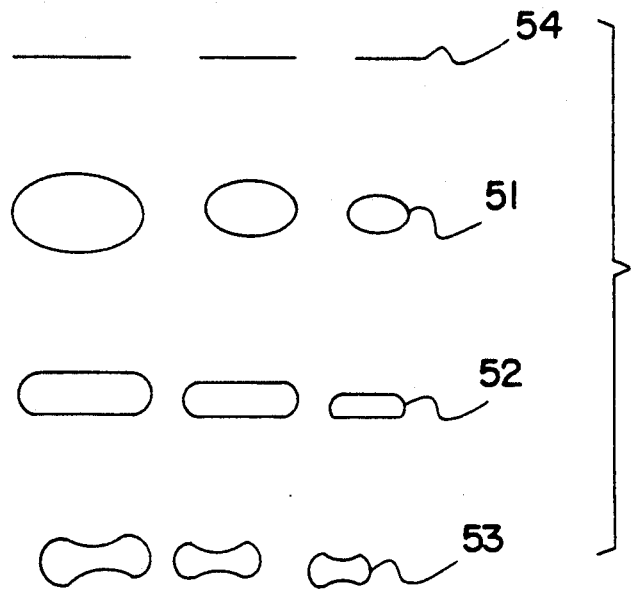
FIG. 11 depicts four preformed indices to be imprinted or impressed on the oral barrier drape alveolar ridge constructed in accordance with the present invention for specific tooth shapes.

Referring now also to FIG. 11, four patterns are shown for indices to be inscribed or embossed as tooth perforation guide 3 which outline the locations for removal of the barrier material from the alveolar ridges to expose a tooth or teeth as described in FIGS. 1 through 10 above. The forms or patterns utilized as indices for the perforation guides may be any shape and size, such as dots or dimples, a straight or curved line, rectangular, oval or dumbbell. In the preferred embodiment, an oval pattern 51 would be used for teeth such as cuspids and the airway aperture 22; an elongated oval or rectangular pattern 52 for teeth such as incisors; and a dumbell pattern 53 for teeth such as molars. A straight or curved line pattern 54 would be suitable for smaller teeth and for the saliva ejector perforation guides 23. The dimensions of each index are based on the bucca-lingual and mesial-distal measurements at the neckline or cervix of the various teeth.

Figure 12:
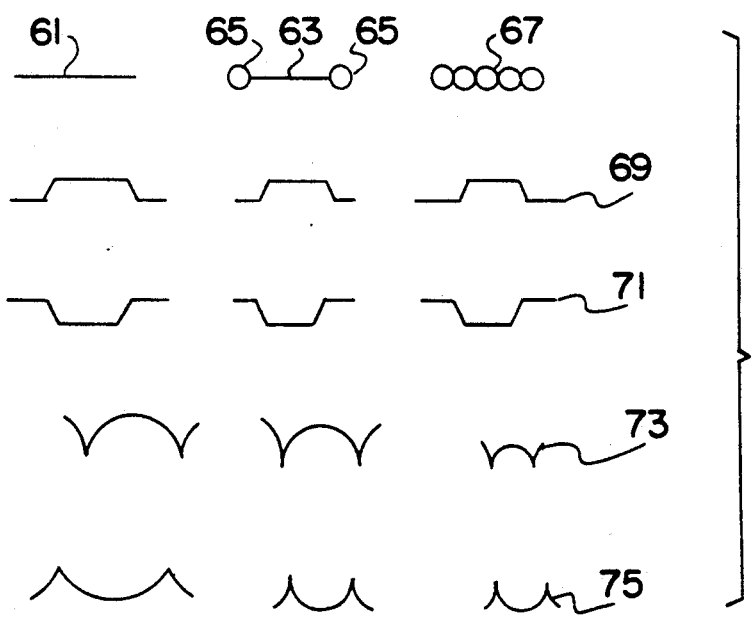
FIG. 12 depicts five suggested patterns for excising the oral barrier drape to expose the tooth (teeth) on which the practitioner will operate.
Figure 13A:
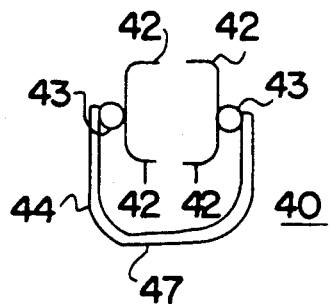
FIGS. 13a, 13b, 13c and 13d illustrate a first embodiment of a tooth clasp retainer device to maintain the oral barrier drape shown in FIG. 1 in position over to a tooth.
Figure 13B:
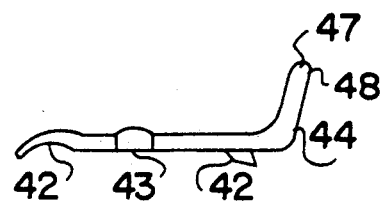
Figure 13C:
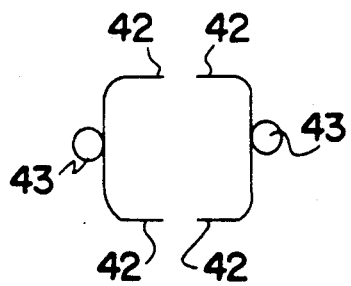
Figure 13D:
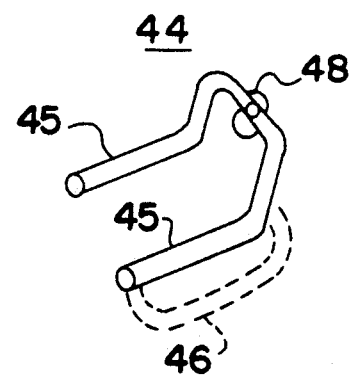
Figure 14A:
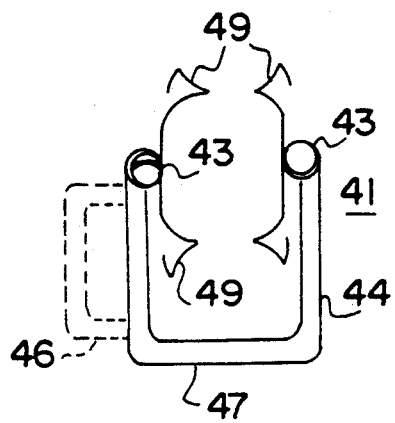
FIGS. 14a, 14b, 14c and 14d illustrate a second embodiment of the tooth clasp retainer device shown in FIG. 13.
Figure 14B:
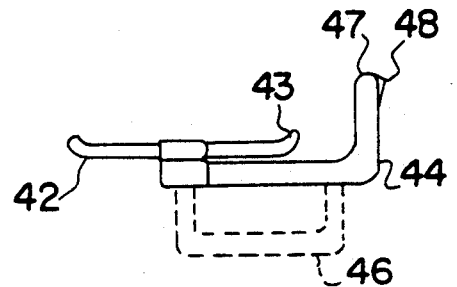
Figure 14C:
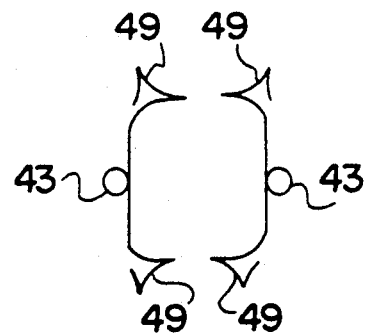
Figure 14D:
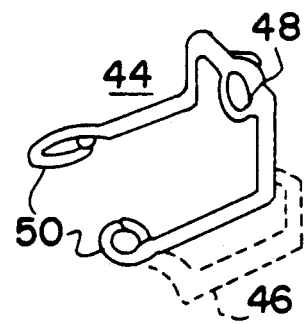

Referring now to FIG. 12, five incision patterns corresponding to the various perforation guide indices shown in FIG. 11 are shown. A curved or straight slit 61 cut from the curve or straight line 54 can be formed with a scalpel or blade (not shown) but tends to tear under tension. To minimize tearing, the slit 63 is terminated with cleanly-cut or punched rounded holes 65. Such termination holes 65 may be punched with well-known rubber dam punches (not shown). Similarly, a straight or curved aperture may be formed by punching a series of interlinking holes 67 for use in situations where the dam material is under tension. The rectangular convex and concave patterns 69 and 71 corresponding to the oval 51, rectangular 52 and dumbbell 53 shaped indices can be cut with a blade or scissors or with a plier-type punch having selectable die faces each shaped for a particular pattern and correspondingly shaped die cavities having cutting edges (not shown). Similarly, the convex and concave patterns 73 and 75 may be cut using scissors or the above-identifed, selectable die face plier-type punch.

For use during dental procedures, the barrier drape 10 of the present invention requires preformed spring retainer devices to retain the barrier drape 10 in its desired position in a patient's mouth. The tension present in the material of prior art rubber dams required strong C-type clamps which gripped the patient's teeth to hold the rubber dam in place. However, the or barrier drape 10 of the present invention merely lays in the patient's mouth, draped over the upper and lower alveolar ridges and also covering the palate and floor of the mouth, thus resulting in minimal tension in the barrier drape material except for localized tension in the immediate area of the barrier drape where the material has been stretched over a tooth or teeth. This local tension is also minimized by utilizing optimally shaped apertures closely conforming to the shape and size of the tooth or teeth to be exposed (as described hereinabove). Therefore, tissue borne spring retainers which apply pressure to the barrier drape along the base of the alveolar ridges, the upper and low buccal vestibules, the palate and floor of the mouth and, in some cases, the lips, hold the barrier in position against the contours of the oral cavity. The tooth borne retainers may also include free end tips designed to protrude into the interproximal spaces between the teeth clasp a tooth thus providing both vertical and horizontal retention of the barrier drape material and maintaining the barrier material in close adaptation to the exposed teeth while avoiding damage to the teeth and soft tissues of the gum and mouth.

Referring now to FIGS. 13 and 14, various forms of barrier drape spring retainers or tooth borne clasps for retaining a barrier drape manufactured in accordance with the present invention in position over a tooth are shown. A first embodiment of the performed spring retainer device as shown in FIGS. 13a-13d comprises interproximal free end arms 42 formed with central loop 43 centrally located therebetween forming a C-shaped member. A pair of the C-shaped members disposed in facing relationship by connector arch 44 form a clasp 40 suitable for use with an individual tooth. The interproximal free end arms 42 protrude into the interproximal spaces between the teeth and below the crowns of the teeth by the spring action of connector arch 44. Connector arch 44 is sized to be slightly smaller than the tooth upon which the clasp 40 is intended to be installed, thus providing sufficient pressure to retain the barrier drape in close contact with the neckline of the tooth yet gentle enough pressure to avoid injury to the teeth and gum tissue. Central loops 43 provide an attachment point should additional appliances (not shown) be desired and further serve as installation and retrieval grasping aids to be utilized with dental pliers or forceps (not shown). Connector arch 44 has two lateral arms 45 to which lateral loop skirts 46 may be attached to provide stability. The crown 47 of connector arch 44 may be plain as in FIG. 13a or possess a crown loop 48 providing additional spring action as in FIG. 13d. Connector arch 44 is connected at the maximum convexity of the central loop 43 of the interproximal free end arms 42 as shown in FIG. 13a.

A second embodiment of the retaining clasp 41 as shown in FIGS. 14a-14d comprises a pair of opposing C-shaped members 41 having triangular interproximal free end arms 49 designed to more closely approximate the configuration of the interproximal spaces between the teeth. The triangularly formed end arms 49 are fabricated from a resilient material so as to be compressible thereby accommodating interproximal spacing of varying widths. Lateral arm end loops 50 on the free ends of the connector arch 44 provide connection means so that the lateral arm end loops 50 can be superimposed upon the central loops 43 between the triangular interproximal free end arms 49 so as to provide a continuous opening of the retaining means. Connector arch 44 is sized to be slightly smaller than the tooth upon which the clasp 41 is to be attached as described hereinabove.

Figure 15A:
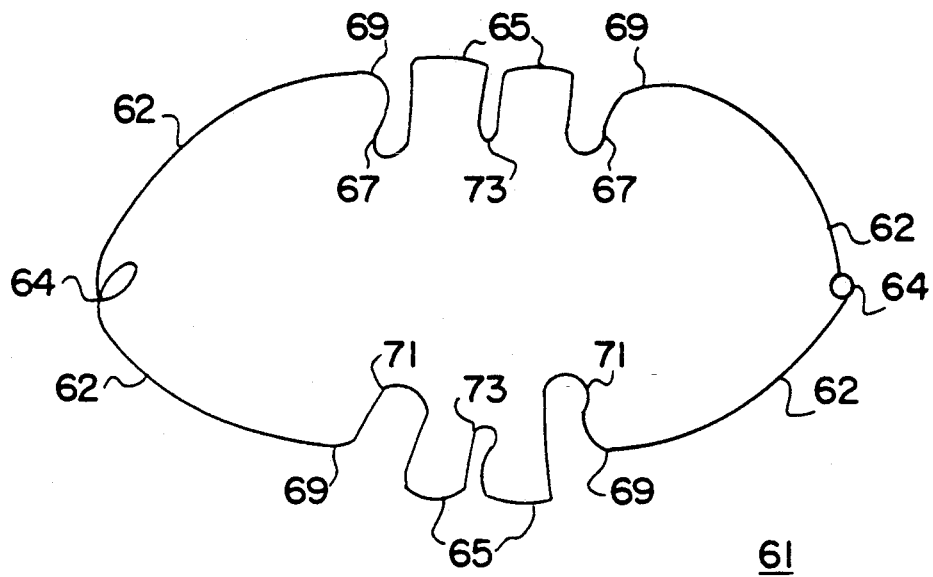
FIGS. 15a and 15b are frontal perspective views of tissue borne vestibular and inside retainer devices, respectively, for maintaining the oral barrier drape device shown in FIG. 1 in position in a patient's mouth.
Figure 15B:
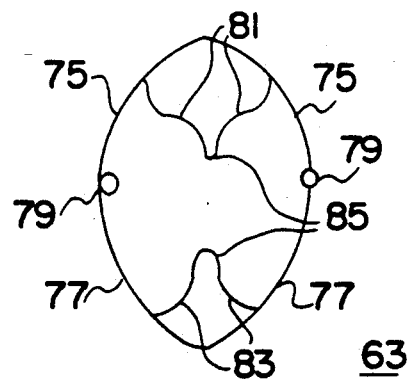
Figure 15C:
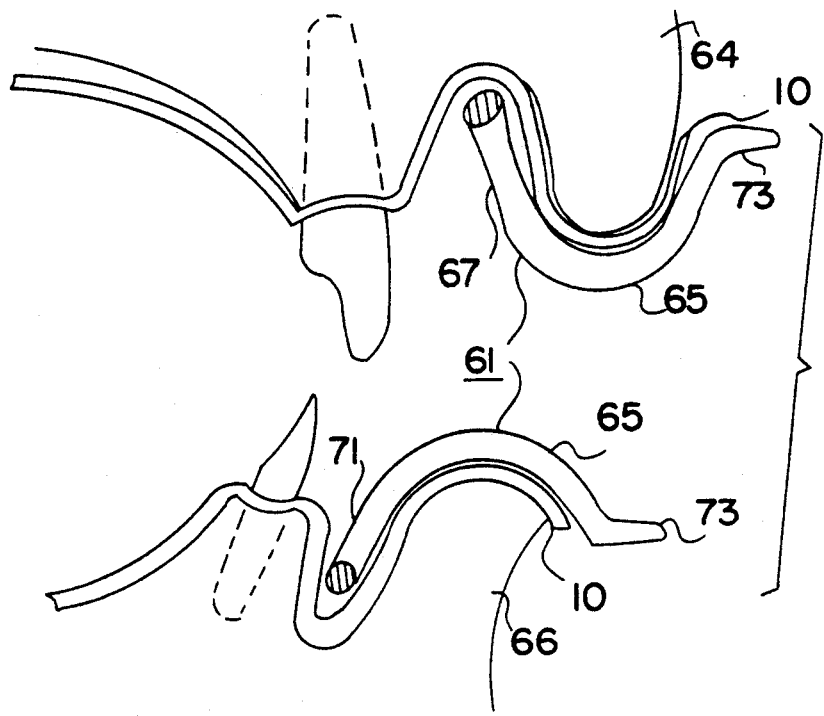
FIGS. 15c and 15d are a side view taken in section illustrating the installation of the oral barrier drape device shown in FIG. 1 retained in position in a patient's mouth utilizing the retainer devices shown in FIG. 15a and 15b, respectively.
Figure 15D:
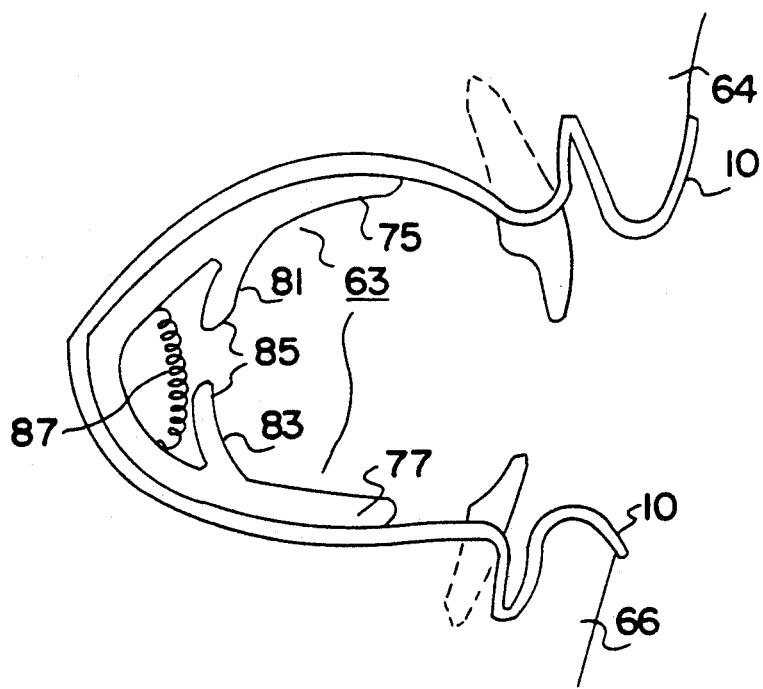

Referring now to FIGS. 15a-15b, a pair of individual full mouth barrier drape retainer spring-loaded devices including a labial-facial or vestibular retainer 61 and a lingual-palatal or inside retainer 63, respectively, are shown. A vestibular retainer 61 fabricated of a molded resilient material such as plastic or rubber, or of resilient wire such as spring steel comprises vestibular arms 62 emerging from angular hinge action coronoid configurations 64 for providing spring-loaded, vertically opening action. Maxillary 67 and mandibular 71, labial-lip flange configurations are formed by a near right angle bend 69, departing from the vestibular arms 62 conforming to the general curvature of the internal aspect of a patient's lip forming vestibular loops 65 curving outwardly over the lip to form a central loop 73 disposed midway between both the maxillary 67 and mandibular 71 flanges. Inside retainer 63 comprises palatal 75 arms and lingual 77 arms emerging from angular hinge action coronoid configurations 79 having angled palatal 81 and lingual 83 arms forming into a centrally located loops 85. FIGS. 15c-15d are cross-sectional views from the side illustrating the installation of an oral barrier drape 10 in a patient's mouth retained in place by the vestibular retainer 61 in combination with the lingual palatal or inside retainer 63. Vestibular loops 65 fit over the patient's upper and lower lips 64, 66 to retain the barrier drape 10 in position. Central loops 73 in the vestibular retainer 61 and central loops 85 in the inside retainer 63 engage the jaws 91 of forceps 89 as shown in FIG. 15e for compression of the retainer 61, 63 allowing quick and efficient placement and removal of the retainers 61, 63 in a patient's mouth. The spring action of the retainers 61, 63 necessary to retain the barrier drape 10 in position results from the resiliency of the vestibular material which the retainers 61 and the lingual plate retainer 63 are fabricated from and from the form of the hinge action coronoid configurations 64, 79, respectively, where the upper and lower coronoid portions are joined. If the retainers 61, 63 are molded from a suitable material such as resilient plastic, the coronoid configuration will be a flat or rounded bend. When using resilient wire, a coil (as shown in FIGS. 15a-15b), clamps, soldering or other means of joining the upper and lower coronoid members and forming the coronoid configurations may be employed. As shown in FIG. 15d, coil springs 87 may be attached between the upper and lower coronoid members to provide additional spring pressure. Resilient wire retainers may be coated with plastic, rubber or other suitable elastomeric material by dipping or other suitable coating process to provide additional spring action and cushioning. Alternatively, the various wire members of the retainer devices may be enclosed in soft rubber or plastic tubing to provide cushioning.

Referring now to FIGS. 16a and 16b, a combined form 95 of the vestibular and the inside retainers described above is shown. The combined form 95 is fabricated of resilient wire, such as spring steel wire, in which the coronoid configurations 101 may be formed by twisting 101 of the vestibular arms 103 with the maxillary 105 and mandibular 107 arms of the inside retainer. FIG. 16b illustrates independent maxillary form 111 composed of the maxillary portion of the vestibular arm 113 and the maxillary arm 115 of the inside retainer which end in a rectangular form 117, and an independent mandibular form 121 composed of the mandibular vestibular arm 123 and the mandibular arm 125 of the inside retainer which end in a rectangular form 119. To achieve the combined form 95 the rectangular ends of 117, 119 of the individual maxillary 111 and mandibular 121 forms, respectively, are joined by welding, soldering, clamping or other suitable means to form the coronoid configuration 127.

Figure 17A:
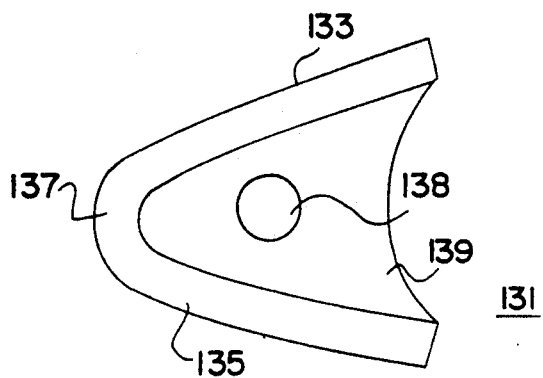
FIGS. 17a-17c are a side view in perspective of several forms of an occlusal wedge constructed in accordance with the principles of the present invention.
Figure 17C:
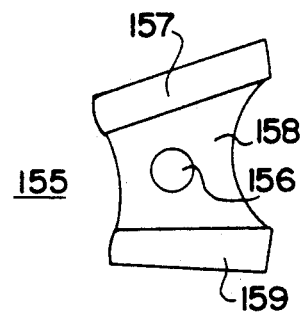
Figure 17B:
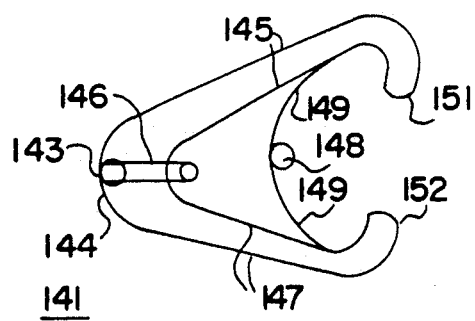

Referring also now to FIGS. 17a and 17b, the independent forms 111, 121 may be positioned on a patient's respective jaws over the oral barrier 10 and held in place through the use of occlusal wedging devices 131 corresponding to the triangular form of the occlusal planes of the upper and lower teeth with the mouth partially opened. An occlusal wedge 131 is preferably made of a suitable elastomeric material possessing maxillary arms 133 and mandibular arms 135 hinged together at 137, either integrally or by well-known joining means and possessing an integral web 139 which may include an opening 138 to retain a suction device, such as a saliva ejector. Similarly, occlusal wedge 141 may be fabricated of resilient wire with the coronoid configuration 143 formed by the maxillary arms 145 and the mandibular arms 147 being joined together by means of loops 144 joined by a crosspiece 146. A center spring 149 employing a loop 148 provides additional spring action and a means of attaching a saliva ejector and joins the maxillary occlusal stop 151 to the mandibular occlusal stop 152.

Figure 17D:
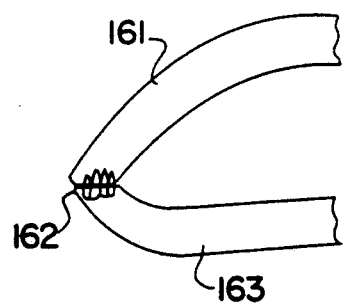
FIG. 17d is a side view in perspective of a partial resilient wire retainer device.

Referring now also to FIGS. 17c and 17d, a second embodiment of an occlusal wedge 155 as shown. The occlusal wedge 155 comprises hollow maxillary tubes 157 and hollow mandibular tubes 159 joined together by web 158 to form a triangular shape corresponding to occlusal planes of the upper and lower teeth. Maxillary free arm 161 and mandibular free arm 163 which may be joined at coronoid configuration 162 are telescoped through the corresponding hollow tubes 157, 159, respectively. The webbing 158 may or may not include an opening 157 or other mounting means for attaching a saliva ejector or other device.

Figure 18A:
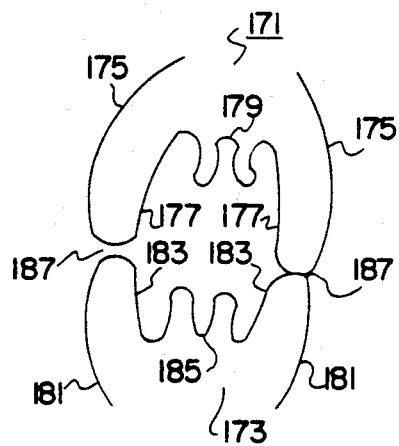
FIG. 18a is a front view of another embodiment of the resilient wire retainer device according to the principles of the present invention.
Figure 18B:
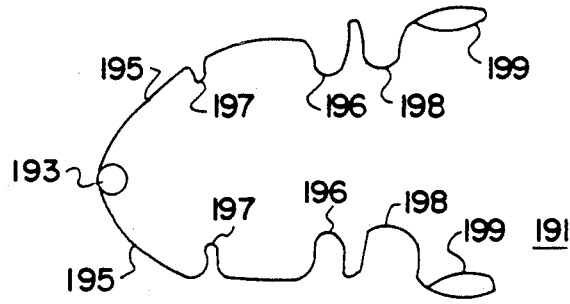

Referring now to FIGS. 18a and 18b, another embodiment of performed dental barrier drape 175 retainer devices comprises a resilient wire maxillary form 171 having maxillary free arms 175 and continuous palatal arms 177 with a distally inclined notch 179, and a resilient wire mandibular form 173 having mandibular free arms 181 and continuous lingual arms 183 with a distally inclined notch 185. The maxillary and mandibular forms 171, 173 may be used individually as with the previously described occlusal wedge 131 or in combination joined at the coronoid configuration 187 as described hereinabove. When the combined form, i.e., the maxillary arms 175, 177 joined to the mandibular arms 181, 183 at the coronoid configuration 187, is utilized the retainer is inserted in and removed from the patient's mouth by using the forceps 89 shown in FIG. 15e, the rounded jaws 91 being inserted into the notches 179, 185, the jaw notches 92 engaging the wire of the notches 179, 185 thus permitting compression of the maxillary and mandibular joined forms 171, 173. FIG. 18b illustrates a spring accessory device 191 fabricated of a single piece of resilient wire, including coil 193 from which extend two arms 195 each incorporating notched half loops 197, incisal stop loops 196, lip loops 198, ending in larger closed loops 199 that act as handles for placing and removing the spring accessory devie 191. Notched loops 197 mate with the maxillary and mandibular retainer device 171, 173 inclined notches 179, 185 and thus stabilize the retainer devices 171, 173 when used individually; i.e., the maxillary arms 175, 177 are not joined to the mandibular arms 181, 183 at coronoid configuration 187. When being used, the spring accessory device 191 also acts as a means to encourage the mouth to remain open. To provide free and unimpeded access to the anterior teeth, the arms 195 may be bent forward of the arm notches 197 at a desired angles so that the handle loops 199 are disposed at the sides rather than front of the patient's mouth.

Figure 19A:
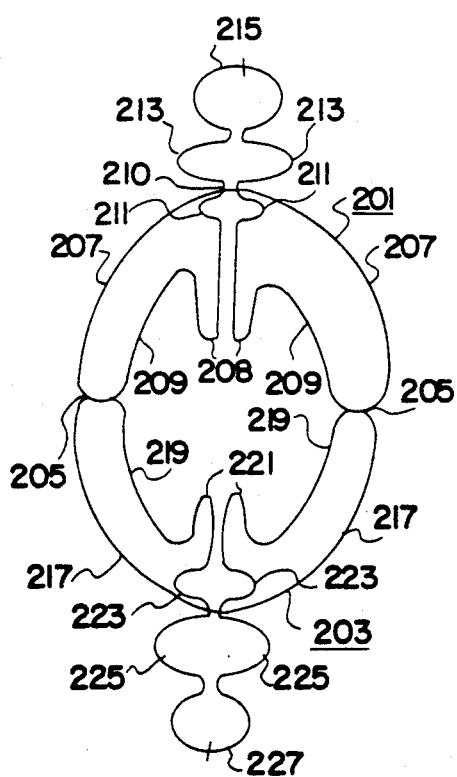
FIGS. 19a and 19b are a front view of another embodiment of the resilient wire retainer devices according to the principles of the present invention.
Figure 19B:
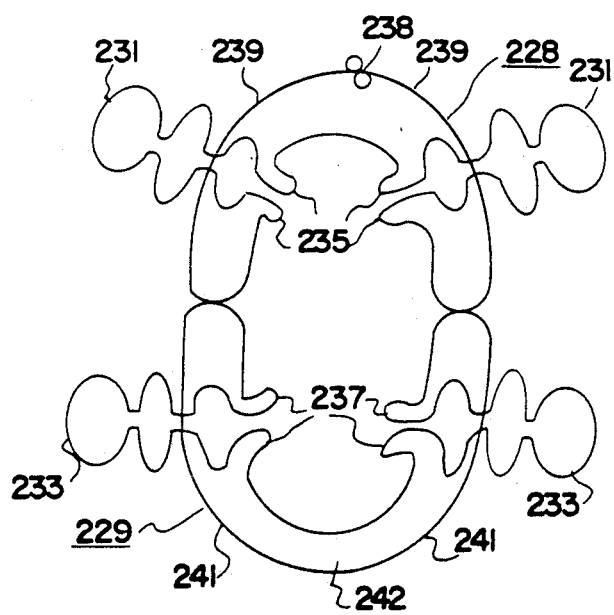
Figure 19C:
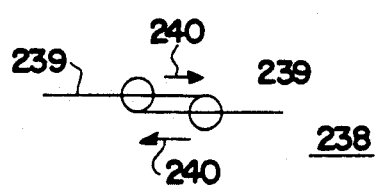

Referring now to FIGS. 19a-19c, 19a is a front perspective view of individually formed maxillary and mandibular retainers 201, 203, respectively, which are joined in the coronoid configuration 205. The maxillary retainer 201, which anticipates free access to the posterior teeth, comprises a continuous vestibular arm 207 and continues into the palatal arms 209, which may include palatably located adjustment loops 208 and which continue anteriorly to form tooth stop loops 211 half-looping under and over the vestibular arm 207 at 210 on either side of the adjustment loops 208 into reverse half loops 213 that accommodate the upper lip contour, then reversing again to a horizontal plane to form horizontal half loops 215 that are joined at their ends to act as a handle. The mandibular retainer 203 is a mirror image form of the maxillary retainer 201 comprising vestibular arms 217 corresponding to 207, lingual arms 219 corresponding to 209 and adjustment loops 221, tooth stop loops 223, lower lip contour loops 225 and handle 227 as described. FIG. 19b is a front perspective view illustrating a modification 228, 229 of the retainers 201, 203, respectively, which anticipates free access to the anterior teeth. Bilateral maxillary 231 and mandibular 233 placement-removal handle forms, comparable to the centrally located handle forms 215, 227, respectively, including adjustment loops 235, 237 are disposed at the sides of the retainers 228, 229, respectively, to extend from the sides of the patient's mouth rather than the front of the mouth. The maxillary vestibular arms 239 are joined by means of a sliding loop connection 238, better shown by movement arrows 240 in FIG. 19c. Similarly, the mandibular vestibular arms 241 are joined by sliding loop connection 242.

Figure 20A:
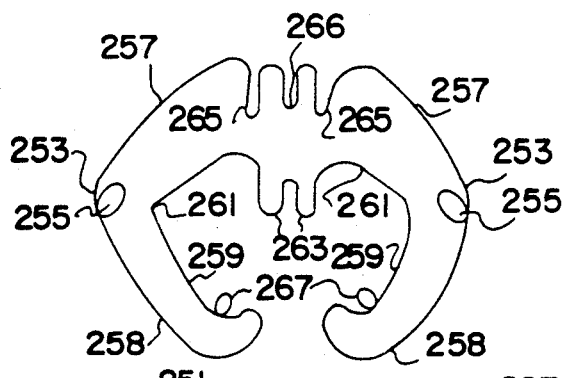
FIG. 20a is a front view of another embodiment of the resilient wire retainer devices according to the principles of the present invention.
Figure 20B:
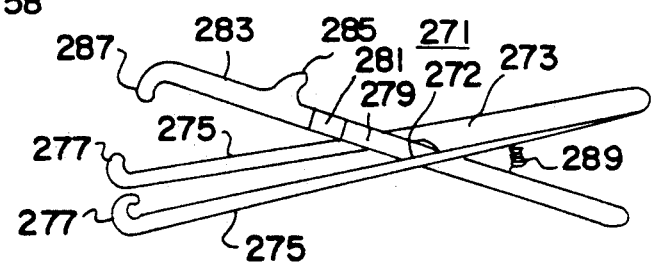

Referring now to FIGS. 20a and 20b, FIG. 20a is a front perspective view illustrating another embodiment of a resilient wire form of the barrier retainer comprising coronoid configurations 253 having bilateral coils 255 formed in the maxillary and mandibular vestibular arms 257, 258, respectively, with the mandibular vestibular arms 258 being formed into mandibular lingual arms 259 which continue to form the maxillary palatal arms 261 connected by bilateral adjustment loops 263. The maxillary vestibular arms 257 continue from the bilateral coils 255 forward to form into bilateral labial adjustment loops 265 with a central loop 266 formed therebetween. The retainer form 251 can be modified to employ a similar handle formation as shown in FIGS. 19a and 19b to allow compression of the retainer device 251 for insertion and removal from the patient's mouth. FIG. 20b illustrates a forceps device 271 which may be used to efficiently insert and remove the retainer 251 shown in FIG. 20a. The forceps device 271 comprises a shank 273 bifurcated into two arms 275 having a curved jaw 277 at the distal ends thereof designed to be inserted into and engage mandibular placement-removal loops 267 of the barrier retainer 251. The shank 273 being hingably joined at the bifurcation point 272 to a second shank 279 having lengthwise sliding adjustment feature 281 that permits the forward separable portion 283 of the shank 279 to be adjusted lengthwise forwards and backwards by an integral finger grip 285 to position the jaw 287 to engage the maxillary loop 266 of the retainer 251. A coil spring 289 disposed between the forcep handles 291 maintains the forcep jaws 277, 287 in an open configuration. With the forcep jaws 277, 287 engaging the mandibular placement-removal loops 267 and the maxillary central loop 226, the retainer 251 may be compressed into a more horizontal plane thus permitting the easy and efficient placement and removal of the retainer 251 in a patient's mouth.

Figure 21:
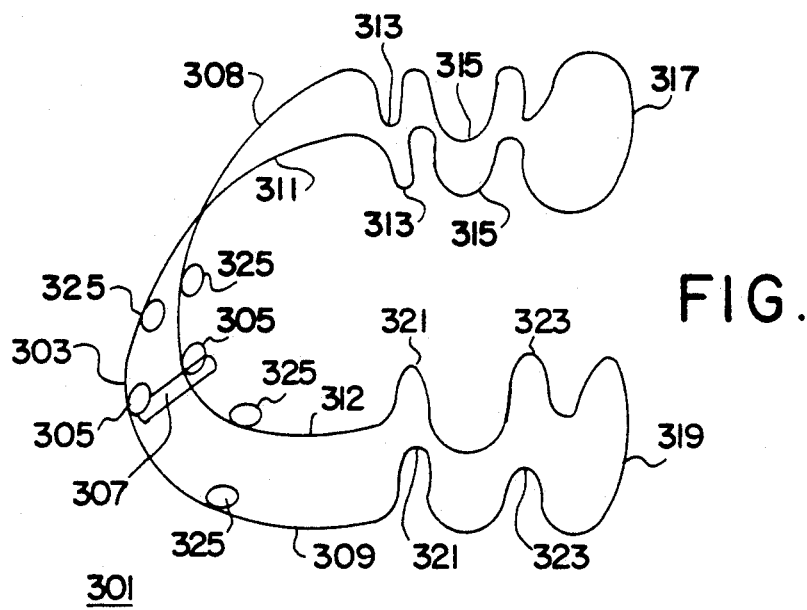
FIG. 21 is a side view in perspective of a resilient wire retainer device according to the principles of the present invention to be used in the right side of a patient's mouth.

Referring now to FIG. 21, a side perspective view of another embodiment of the barrier retainer device of the present invention is shown. Resilient wire retainer 301 is described with respect to the right side of a human mouth and comprises coronoid configuration 303 including coils 305 spaced and joined by wire link 307 to maintain the desired postero-lateral distance between the maxillary 311 and mandibular 309 vestibular arms and the palatal 308 and lingual 312 arms. The maxillary vestibular arms 308 continue anteriorly (forward) having the same configuration as described with reference to FIG. 19a in which there are incisal teeth stop loops 313 that lead into the lip configuration loop 315 then deflect laterally to form horizontal half loops that are joined to form a loop handle 317. Similarly, the mandibular 309 and the lingual 312 free end extensions are shaped to form the mandibular incisal teeth stop loops 321, lip loop 323 and horizontal half loops to form the handle 319. The retainer 301 as shown is designed for use in either the right side or the left side of a patient's mouth. The incisal teeth stop loops 313 on the maxillary arm 311 and 321 on the mandibular arm 309 may be eliminated for a retainer 301 suitable for use only in the right side of a patient's mouth. Similarly, a mirror image (not shown) of the modified retainer 301 is suitable for the left side of the mouth. The coronoid configuration 303 of the retainer 301 may be modified to join the maxillary and mandibular sections together by other methods, such as by twisting, described hereinabove. Further, the maxillary arms 301, 311 and mandibular arms 309, 312 may include additional coils 325, as shown, to provide additional action. A similar form (not shown) can be employed to retain the barrier drape around the anterior arches as well.

To use the dental barrier drape or rubber dam of the present invention, the desired form of barrier drape 10 (as shown in FIGS. 1-12) is selected and a rubber dam punch or other suitable means as described hereinabove is used to cut apertures in the alveolar ridges 1,2 by punching or cutting out shaped openings outlined by the tooth perforation guides 3 according to the teeth desired to be exposed. If it is desired to expose both teeth and gums, scissors having curved jaws can be used to trim away the desired area of exposure by removing additional material from around the periphery of the previously punched apertures. The preformed punched barrier drape form is then folded along dashed-line 15 and fitted and adapted to the anatomy of the patient's oral cavity, and the septum or material remaining between the punched apertures is carried beneath the contact points of the teeth to be exposed. If additional apertures are desired to provide an air passage to compensate for an impeded nausea respiratory function or for the placement of saliva removal devices or other appliances, the oral barrier drape device is pinched together in the area of the appropriate perforation guide 22, 23 and a pair of curved scissors used to remove the desired marked areas with a semi-lunar cut so that when the oral barrier drape is released a round or elliptical opening has been created through the barrier drape. Since the preformed oral barrier drape conforms to the anatomical features of the patient's mouth, the practitioner can easily manipulate the barrier drape to properly expose the desired teeth or operating area with ease and convenience with any excess barrier drape material neatly placed in appropriate areas so as to not interfere with the insertion and following dental procedures.

When the oral barrier drape form has been properly positioned in the patient's mouth and the desired teeth or operating area exposed, an appropriate retainers or clasps (FIGS. 13-21) are selected and positioned in the patient's mouth within the confines of the barrier (as shown in FIGS. 15c and 15d). The installed retainers depress the oral barrier drape into the concavities of the vestibular areas between the alveolar ridge and the cheeks and lips and into the palatal and lingual concavities of the oral cavity to retain the oral barrier drape in position and to stabilize it. If additional retention, or a special isolation, is desired or required, then the oral barrier drape lends itself to the usage of additional ordinary rubber dam clamps ligatures, or other forms of resilient or ridged edges. For the large majority of routine dental operations, the conforming nature of the oral barrier and the minimal tension present in the barrier material, the barrier retainers constructed according to the present invention are more than adequate to satisfy the retention requirements of the oral barrier constructed in accordance with the present invention.

While the present invention has been particularly shown and described with respect to certain preferred embodiments thereof, it should be readily apparent to those of ordinary skill in the art that various changes and modifications in form and details may be made without departing from the spirit and scope of the invention as set forth in the appended claims.

I claim:

1. A dental retainer device for retaining a dental barrier drape in position in a patient's mouth when installed therein, said dental barrier device comprising:
   an upper shaped member preformed to conform generally to the outline of the base of an upper alveolar ridge in a patient's mouth;
   a lower shaped member preformed to conform generally to the outline of the base of an opposing lower alveolar ridge in a patient's mouth;
   means joining said upper and lower shaped members together at a rearward end of each of said shaped members, said joined upper and lower members forming a generally C-shaped structure having the apex of the C towards the rear of the patient's mouth behind the endpoint of the respective alveolar ridges when said retainer device is installed in the patient's mouth, said means including resilient means providing a spring force urging said upper and lower members radially upwardly and downwardly, respectively, from said apex, said upper and lower members pressing against the upper and lower anatomical features of the patient's mouth thereby retaining a dental barrier drape in position when said dental barrier drape is installed in a patient's mouth and disposed between said upper and lower members, respectively, and said anatomical features.

2. A dental retainer device as in claim 1 wherein said upper and lower shaped members, respectively, each include a shaped partial loop conforming generally to the shape of a tooth in the respective upper and lower alveolar ridge at a predetermined position, said shaped partial loop forming a tooth stop for retaining said dental retainer device in a desired position with respect to the upper and lower alveolar ridges in a patient's mouth.

3. A dental retainer device as in claim 2 wherein said upper and lower shaped members, respectively, each include a shaped partial lip loop conforming generally to the shape of the upper and lower lips of a patient's mouth, said lip loops including generally flat portions protruding from the patient's mouth when installed therein and forming handle portions allowing said C-shaped dental retainer device to be compressed for installation in and removal from the patient's mouth.

4. A dental retainer device as in claim 1 wherein said C-shaped dental retainer device comprises a wire structure.

5. A dental retainer device as in claim 4 wherein said upper and lower shaped members, respectively, each include a shaped partial loop at a forward end thereof, said shaped partial loop protruding from a patient's mouth when said dental retainer device is installed therein, said upper and lower shaped partial loops forming a retainer handle allowing said dental retainer device to be compressed for installation in and removal from a patient's mouth.

6. A dental retainer device as in claim 5 wherein said wire structure is fabricated from stainless steel spring wire.

7. A dental retainer device as in claim 5 wherein said wire structure is coated with a coating of an elastomeric material for providing additional spring action and cushioning.

8. A dental retainer device as in claim 1 wherein said resilient means comprises spring means disposed between said upper and lower members for providing a force urging said upper and lower members away from one another and against said dental barrier drape thereby retaining said dental barrier drape in position.

9. A dental barrier drape comprising a thin membrane of flexible resilient material including at least one preformed configuration conforming to the contours of at least a portion of an alveolar process and associated anatomical structures of the mouth and oral cavity.

10. A dental barrier drape as in claim 9 including preformed first and second raised curved portions conforming to the upper and lower alveolar ridges in the human oral cavity, respectively, having integral tooth perforation guides formed along the dorsal portion of said first and second raised curved portions, said tooth perforation guides corresponding to the locations of teeth over which said first and second raised curved portions overlay when said dental barrier drape is inserted into the mouth and positioned in the oral cavity.

11. A dental barrier drape as in claim 10 including at least one first perforation guide formed therein for providing an aperture therethrough for receiving an evacuation or aspiration device.

12. A dental barrier drape as in claim 11 including a second perforation guide formed therein for providing a patient breathing aperture therethrough.

13. A dental barrier drape as in claim 10 further including:
   a palatal concavity formed and disposed medially within the curve of said first raised curved portion, said palatal concavity conforming generally to the palatal area of a maxilla of the oral cavity, said palatal concavity extending into the adjacent base of said first raised curved portion;
   a maxillary labial-buccal vestibule concavity formed at the outside base of said first raised curved portion and extending radically outwardly towards said shaped perimeter, said maxillary labial-buccal vestibule concavity conforming generally to the maxillary labial-buccal vestibule of the oral cavity;
   a mandibular labial-buccal vestibule concavity formed at the outside base of said second raised curved portion and extending radially outwardly towards said shaped perimeter, said mandibular labial-buccal vestibule concavity conforming generally to the mandibular labial-buccal vestibule of the oral cavity; and a lingual trough formed about the inside base of said second raised curved portion extending radially inwardly rising to form a lingual convexity, said lingual convexity disposed medially within said second raised curved portion and generally conforming to the floor of the oral cavity providing space for the tongue, said lingual convexity blending into the distal portion of said palatal concavity and extending outwardly between the open, distal ends of said first and second raised curved portions to said perimeter.

14. A dental barrier drape as in claim 13 wherein said maxillary labial-buccal vestibule concavity and said mandibular labial-buccal vestibule concavity incorporates a flexible malleable material disposed around portions of the base of said concavities for maintaining the desired arch curvature conforming to the underlying adjacent alveolar ridge.

15. A dental barrier drape as in claim 13 further including concavities formed therein conforming to the region of the coronoid ridge of the mandible and the hamular notch area of the maxilla permitting the passive folding of said dental barrier drape during insertion and placement thereof in the oral cavity.

16. A dental barrier drape as in claim 10 further comprising a perimeter support means integrally formed at said membrane perimeter.

17. A dental barrier drape as in claim 16 wherein said perimeter support means comprises a perimeter support frame formed of malleable material embedded in said thin membrane material about the length of said shaped perimeter.

18. A dental barrier drape as in claim 10 further comprising an alveolar support means integrally formed about the base of said first and second raised curved portions.

19. A dental barrier drape as in claim 18 wherein said alveolar support means comprises an alveolar support frame formed of malleable material embedded in said thin membrane material at the base portion about the outside of said first and second raised curved portions, said alveolar support frame selectively formable to facilitate a closer conformation to the alveolar ridges in an individual human oral cavity.

20. A dental barrier drape as in claim 10 wherein each said integral tooth perforation guide is sized and shaped to conform to a corresponding tooth at said corresponding location, said dental barrier device adapted to be slipped over and around selected corresponding teeth when said corresponding tooth perforation has been incised exposing said selected tooth or teeth, said membrane material fitting tightly about said exposed tooth at neckline.

21. A dental barrier drape as in claim 20 further comprising barrier retaining means adapted to secure and retain said dental barrier drape in position when installed in a human oral cavity.

22. A dental barrier drape as in claim 21 wherein barrier retaining means comprises a wire structure including a pair of spaced jaws adapted to grasp an exposed tooth at said tooth's neckline, each of said jaws including at least one free end adapted to protrude into the interproximal spaces beneath the contact points of adjacent teeth, said jaws connected by an arch of resilient wire providing a force urging said jaws inwardly towards one another.

23. A dental barrier drape as in claim 21 wherein said barrier retaining means comprises:

a first frame having at least one arch member having a shape congruent to the upper alveolar ridge in the oral cavity, said first frame adapted to be positioned over said dental barrier drape adjacent said first preformed curved portion;

a second frame having at least one arch member having a shape congruent to the lower alveolar ridge in the oral cavity, said second frame adapted to be positioned over said dental barrier drape adjacent said second preformed curved portion; and resilient means disposed between and coupling said first and second frames together, said resilient means providing a force urging said first and second frame away from one another and against said dental barrier drape, portions of said dental barrier drape being urged against portions of the interior structure of the oral cavity and maintained in position in the oral cavity.

24. A dental barrier drape as in claim 21 wherein said barrier retaining means comprises:

an outer retainer comprising:

an upper frame having at least one arch member having a shape generally congruent to the outer outline of the base of the upper alveolar ridge in the oral cavity, said upper frame adapted to be positioned over said dental barrier drape adjacent said first preformed curved portion;

a lower frame having at least one arch member having a shape generally congruent to the outer outline of the base of the lower alveolar ridge in the oral cavity, said lower frame adapted to be positioned over said dental barrier drape adjacent said second preformed curved portion; and resilient means disposed between and coupling said upper and lower frames together, said resilient means providing a force urging said upper and lower frame away from one another and against said dental barrier drape, portions of said dental barrier drape being urged against portions of the oral cavity interior structure outboard of said upper and lower alveolar ridges; and an inner retainer comprising:

an upper frame having at least one arch member having a shape generally congruent to the inner outline of the base of the upper alveolar ridge in the oral cavity and adapted to conform to the roof of the oral cavity interior of said upper alveolar ridge, said upper frame adapted to be positioned over said dental barrier drape adjacent said first performed curved portion;

a lower frame having at least one arch member having a shape generally congruent to the inner outline of the base of the lower alveolar ridge in the oral cavity and adapted to conform to the floor of the oral cavity interior of said lower alveolar ridge, said lower frame adapted to be positioned over said dental barrier drape adjacent said second preformed curved portion; and resilient means disposed between and coupling said upper and lower frames together, said resilient means providing a force urging said upper and lower frame away from one another and against said dental barrier drape, portions of said dental barrier drape being urged against portions of the oral cavity interior structure inboard of said upper and lower alveolar ridges; and said dental barrier drape disposed between said outer and inner retainers, respectively, and the interior anatomical features of the oral cavity.

25. A dental barrier drape as in claim 10 wherein integral beading having a preformed geometric cross-section shape is disposed around the sides of said curved raised portion below the neckline level of exposed teeth for providing additional seal of said dental barrier drape on the underlying alveolar ridge.

26. A dental barrier drape as in claim 25 wherein said beading comprises thickened areas of said barrier material formed in preformed geometric cross-section shape.

27. A dental barrier drape as in claim 10 wherein a flexible malleable material is embedded in said dental barrier drape located around the sides of said curved raised portion below the neckline level of exposed teeth allowing manipulation following placement for providing additional seal of said dental barrier drape on the underlying alveolar ridge.

28. A dental barrier drape as in claim 10 comprising peripheral cutaways of said shaped periphery for accommodating facial features of a patient.

29. A dental barrier drape as in claim 9 including at least one raised curved portion, said raised curved portion conforming to a selected portion of an upper or lower alveolar ridge in the oral cavity, said raised curved portion having integral tooth perforation guides formed along the dorsal portion thereof, said integral tooth perforation guides corresponding to selected teeth locations on said selected portions of the upper or lower alveolar ridges over which said raised curved portion overlays when said dental barrier device is inserted and positioned in a the oral cavity.

30. A dental barrier drape as in claim 29 wherein each of said tooth perforation guides is sized and shaped to conform to an associated tooth located at said corresponding location, said dental barrier drape adapted to be slipped over and around selected teeth when the barrier material is removed from said associated tooth perforation guides thereby exposing said selected teeth, said membrane material fitting tightly around the neckline of each of said exposed teeth when said dental barrier drape is inserted and positioned in the oral cavity.

* * * * *

UNITED STATES PATENT AND TRADEMARK OFFICE
CERTIFICATE OF CORRECTION

PATENT NO. : 5,078,604
DATED : January 7, 1992
INVENTOR(S) : Oscar Malmin It is certified that error appears in the above-identified patent and that said Letters Patent is hereby corrected as shown below:

Title page, under the heading "ABSTRACT," line 6, delete "pateint's" and substitute therefor --patient's--.

In Column 6, line 36, delete "1b141d" and substitute therefor --1b-1d--.

In Column 12, line 47, delete "devie" and substitute therefor --device--.

Signed and Sealed this

Twenty-fifth Day of May, 1993

Attest:

MICHAEL K. KIRK

*Attesting Officer*     Acting Commissioner of Patents and Trademarks